United States Patent [19]

Inoue et al.

[11] Patent Number: 5,087,751
[45] Date of Patent: Feb. 11, 1992

[54] METHOD OF PREPARING OPTICALLY ACTIVE 3,4-DIHYDROXY BUTYRIC ACID DERIVATIVES

[75] Inventors: Kenji Inoue, Hyogo; Mitsunori Matsumoto, Nakatsu; Satomi Takahashi, Kobe, all of Japan

[73] Assignee: Kanegafuchi Kagaku Kogyo K.K., Osaka, Japan

[21] Appl. No.: 610,873

[22] Filed: Nov. 9, 1990

Related U.S. Application Data

[62] Division of Ser. No. 343,565, Apr. 27, 1989, Pat. No. 4,994,597.

[30] Foreign Application Priority Data

Mar. 31, 1989 [JP] Japan ................................ 63-106856

[51] Int. Cl.$^5$ .................. C07C 53/124; C07C 223/09
[52] U.S. Cl. .................... 564/192; 564/201; 564/126; 564/129; 564/130; 562/587
[58] Field of Search ............... 564/192, 201, 126, 129, 564/130; 562/587

[56] References Cited

U.S. PATENT DOCUMENTS 4,851,434 7/1989 Deckner ....................... 564/201

Primary Examiner—David B. Springer
Attorney, Agent, or Firm—Sughrue, Mion, Zinn, Macpeak & Seas

[57] ABSTRACT

The present invention presents a method for preparation of S-3,4-dihydroxy butyronitrile expressed by the structural formula (II)

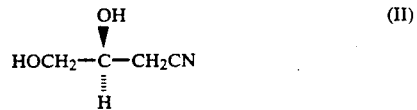

characterized by causing R-3-chloro-1,2-propanediol expressed by the structural formula (I)

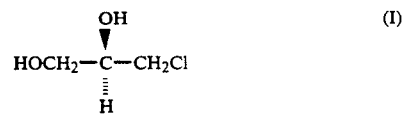

to react with a cyanating agent. According to this invention, optically active 3,4-dihydroxy butyronitrile and 3,4-dihydroxy butyric acid derivatives may be manufactured economically and efficiently.

6 Claims, No Drawings

METHOD OF PREPARING OPTICALLY ACTIVE 3,4-DIHYDROXY BUTYRIC ACID DERIVATIVES

This is a divisional of application Ser. No. 07/343,565 filed Apr. 27, 1989, now U.S. Pat. No. 4,994,597.

BACKGROUND OF THE INVENTION

Field of the Invention

The present invention relates to a method for preparing optically active 3,4-dihydroxy butyronitrile and 3,4-dihydroxy butyric acid derivatives.

Description of the Prior Art

Hitherto the following two methods have been known for the preparation of optically active 3,4-dihydroxy butyric acid derivatives or 3,4-dihydroxy butyronitrile:

(1) The method of reducing dimethyl ester of L-malic acid by using boran dimethyl sulfide in the presence of a catalytic amount of sodium borohydride to convert the same into 3,4-dihydroxy butyric acid methyl ester (Japanese Laid-Open Patent 61-22049, Japanese Laid-Open Patent 63-22056, Chemistry Letters 1389, (1984); and (2) The method of selectively hydrolyzing dimethyl ester of L-malic acid by using esterase (PLE), reducing by using boran dimethyl sulfide, and converting into 3,4-dihydroxy butyric acid methyl ester (Journal of Organic Chemistry, 50, 1145, (1985)).

On the other hand, as the preparation of racemic compounds, the following methods, among others, are known:

(1) The method of producing 3,4-dihydroxy butyronitrile by the reaction of racemic 3-chloro-1,2-propanediol with KCN in water, or successively treating with NaOH and HCl to convert the same into S-butyrolactone derivative (Compt. Rend. 238, 1231, (1954)).

(2) The method of causing recemic 3-chloro-1,2-propanediol to react with NaCN in water, and refining by using an ion exchange resin (J. Am. Chem. Soc., 197, 24, (1985)).

On these methods, the methods of producing optically active compounds use L-malic acid as the starting material also require boran dimethyl sulfide which is a relatively expensive reducing agent, and hence they involve various problems in economy and operation in the practical preparation of optically active 3,4-dihydroxy butyric acid derivatives.

On the other hand, the method of production of racemic 3,4-dihydroxy butyronitrile by cyanation of 3-chloro-1,2-propanediol is likely to produce by-products such as 3,4-dihydroxy amide and 3,4-dihydroxy butyric acid, and is poor in selectivity of reaction, and it involves various problems to be solved in the reaction selectivity, reaction yield and controllability, in the practical preparation of 3,4-dihydroxy butyronitrile.

SUMMARY OF THE INVENTION

It is hence a primary object of the invention to present a method for preparing optically active 3,4-dihydroxy butyronitrile and 3,4-dihydroxy butyric acid derivatives, both economically and efficiently.

Other objects and benefits of the invention will be better understood and appreciated from the following detailed description.

The present inventors intensively researched in order to establish an industrial preparation method of optically active 3,4-dihydroxy butyronitrile and 3,4-dihydroxy butyric acid derivatives, especially their S forms, both economically and efficiently so as to achieve the above objects, and discovered a method of producing S-3,4-dihydroxy butyronitrile and its hydration reaction product or hydrolysis reaction product, S-3,4-dihydroxy butyric amide, S-3,4-dihydroxy butyric acid, selectively in one reaction vessel, by controlling the reaction conditions, by making use of the reaction of a cyanating agent such as NaCN and KCN with R-3-chloro-1,2-propanediol which can be efficiently manufactured by stereo-selective microorganism decomposition of racemic 3-chloro-1,2-propanediol (Japanese Laid-Open Patents 62-122597, 62-158494, 63-36978), thereby completing this invention.

DETAILED DESCRIPTION OF THE INVENTION

A first invention relates to a method of preparation of S-3,4-dihydroxy butyronitrile expressed by the structural

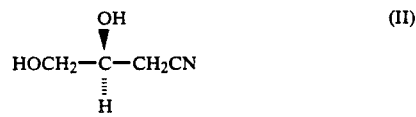

characterized by reaction of R-3-chloro-1,2-propanediol expressed by the structural formula (I)

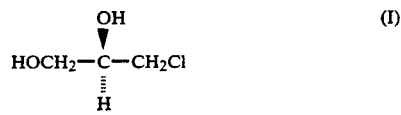

with a cyanating agent;

A second invention relates to a method of preparation of S-3,4-dihydroxy butyric acid amide expressed by the structural formula (III)

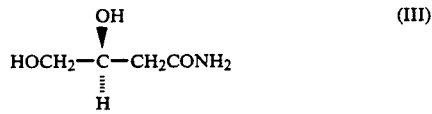

characterized by reaction of R-chloro-1,2-propanediol expressed by the structural formula (I)

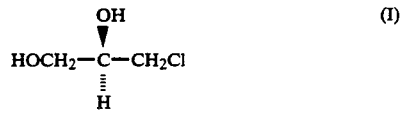

with a cyanating agent in a solvent containing water, and presenting S-3,4-dihydroxy butyronitrile expressed by the structural formula (II)

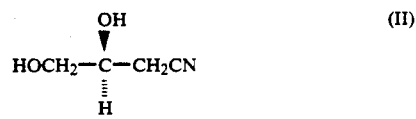

produced in a intermediate process directly to hydration reaction; and

A third invention relates to a method of preparation of S-3,4-dihydroxy butyric acid expressed by the structural formula (IV)

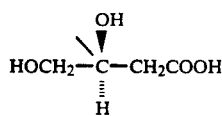  (IV)

characterized by reaction of R-3-chloro-1,2-propanediol expressed by the structural formula (I)

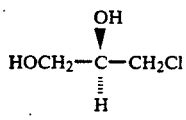  (I)

with a cyanating agent in the presence of a base in a solvent containing water, and directly presenting to hydrolysis.

In the reaction to obtain S-3,4-dihydroxy butyronitrile (II) from R-3-chloro-1,2-propanediol (I), an alcohol, such as methanol and ethanol, and water can be used as a solvent either alone or as a mixture, but in order to minimize the formation of by-products such as 3,4-dihydroxy butyric amide and to enhance the selectivity for formation of 3,4-dihydroxy butyronitrile, it is preferable to perform the reaction in methanol or in a mixed solvent of alcohol and water. As cyanating agents, NaCN, KCN, HCN, MgCN$_2$, AgCN, CuCN, etc., may be used, and in particular, NaCN, KCN and other alkali metal cyanides are preferable from the viewpoint of yield and economy.

The cyanating reaction proceeds only in the presence of an R-3-chloro-1,2-propanediol solvent and a cyanating agent, but the elimination rate of the starting material may be raised and the selectivity of formation of 3,4-dihydroxy butyronitrile may be enhanced by adding a base to the reaction system, for example, NaOH, KOH or other alkali metal hydroxides, amines, etc., or specifically by adding tertiary amines such as triethylamine by 0.1 to 2 equivalents to the reaction system, preferably 0.5 to 1.5 equivalents. Furthermore, by performing reaction by using triethylamine in methanol, more favorable results will be obtained. A proper temperature range for this reaction is 20° to 100° C., but if the temperature is higher, although the elimination of the starting material R-3-chloro-1,2-propanediol is faster, the selectivity of reaction tends to be lower, and in order to obtain 3,4-dihydroxy butyronitrile selectively, it is preferable to agitate for 1 to 40 hours until the starting material is nearly eliminated at 20° to 40° C. For isolation and refining, a mineral acid is added to neutralize the reaction solution, and the solvent is replaced by water, and the solvent is distilled away by extracting continuously by using ethyl acetate or the like, so that an oily matter containing mainly S-3,4-dihydroxy butyronitrile is obtained. To refine further, the object will be achieved by ordinary distillation or column chromatography. However, the reaction and isolation operations are not limited to these methods, but various methods may be employed. The S-3,4-dihydroxy butyronitrile obtained in this way may be easily converted into S-3,4-dihydroxy butyric acid amide and S-3,4-dihydroxy butyric acid by controlling the conditions in the ordinary nitrile hydrolysis conditions.

The reaction for obtaining selectively S-3,4-dihydroxy butyric acid amide from R-3-chloro-1,2-propanediol is effected by using water or a mixture of water and alcohol, preferably water as the solvent, and causing R-3-chloro-1,2-propanediol to react with the cyanating agent such as NaCN, KCN, at 20° to 80° C., preferably 30° to 60° C., while stirring for 1 to 30 hours, preferably 2 to 20 hours. This reaction tends to produce 3,4-dihydroxy butyric acid as a by-product when a base is added to the reaction system or when the temperature is higher than necessary. Isolation and refining operations can be conducted by neutralizing by adding, for example, a mineral acid to the reaction solution, removing the solvent, and performing column chromatography. The amide obtained in this manner may be easily converted into S-3,4-dihydroxy butyric acid in the ordinary conditions for amide hydrolysis.

In the reaction for selectively obtaining S-3,4-dihydroxy butyric acid from R-3-chloro-1,2-propanediol, the object may be achieved by using water or a mixture of water and alcohol, preferably water as the solvent, and stirring at 20° to 100° C., preferably 40° to 80° C., for 30 minutes to 50 hours, preferably 1 to 20 hours, in the presence of the cyanating agent such as NaCN and KCN and preferably a base such as NaOH and KOH by 1 to 3 equivalents, preferably 1 to 1.5 equivalents. Isolating and refining operations can be done by neutralizing the reaction solution by a mineral acid or an ion exchange resin, distilling off the solvent, and performing column chromatography, but the operation of reaction and isolation is not limited to these methods, various methods being also employed.

According to this invention, optically active 3,4-dihydroxy butyronitrile and 3,4-dihydroxy butyric acid derivatives may be produced economically and efficiently.

This invention is further described below while referring to examples and, references examples, but they are not intended to limit the invention in any respect.

EXAMPLE 1

Synthesis of S-3,4-dihydroxy butyronitrile 33.2 g of R-3-chloro-1,2-propanediol and 30.4 g of triethylamine were dissolved in 90 ml of methanol, and 18.6 g of NaCN was added. After stirring for 20 hours at 30° C., concentrated HCl was slowly dropped while cooling the mixture to 0° C. in order to neutralize the excess base, and methanol was distilled away. To the obtained solution, 200 ml of water was added, and extraction was conducted continuously by using ethyl acetate, and the solvent was distilled away, and the obtained oily matter was distilled (B.P. 140° to 150° C./3 mmHg), and finally 25.9 g of S-3,4-dihydroxy butyronitrile was obtained.

$[\alpha]_D^{20} = 24.1$ (C=1.02, CH$_3$OH)

$^1$HNMR (CDCl$_3$, CD$_3$OD): δ2.57–2.73 (m, 2H), 3.62 (d, 2H, J=5 Hz), 3.8–4.13 (m, 1H), 4.5 (bs, 2H), IR (Cm$^{-1}$): (neat) 3400, 2925, 2250, 1415, 1100, 1042

EXAMPLE 2

Synthesis of S-3,4-dihydroxy butyronitrile

After dissolving 18.6 g of NaCN into 90 ml of methanol, a solution having 30.4 g of triethylamine and 33.2 g of R-3-chloro-1,2-propanediol dissolved in 20 ml of methanol was added. After stirring for 6 hours at 40° C., concentrated H$_2$SO$_4$ was slowly added while cooling to 0° C. to neutralize the excess base, and the methanol was distilled away, and 300 ml of acetone was added to the obtained solution. Filtering the precipitating solid, the filtrate was concentrated under reduced pressure, and the obtained oily matter was distilled (B.P. 140° to 150° C./3 mmHg), and finally 24 g of S-3,4-dihydroxy butyronitrile was obtained.

EXAMPLE 3

Synthesis of S-3,4-dihydroxy butyric acid amide

After dissolving 12.36 g of NaCN into 200 ml of water, 50 ml of an aqueous solution of 22.2 g of R-3-chloro-1,2-propanediol was slowly dropped, while stirring for 15 hours at 40° C. The solution was neutralized by concentrated HCl while cooling to 0° C., and $C_2H_5OH$ was added to precipitate an inorganic salt, which was filtered, and the filtrate was concentrated, and the obtained oily matter was refined by column chromatography (acetone) with silica gel, and finally 17.3 g of S-3,4-dihydroxy butyric acid amide was obtained.

$[\alpha]_D^{20} = -15.2$ (C=1.09, $CH_3OH$)

$^1$HNMR ($CDCl_3$, $CD_3OD$): δ2.37-2.53 (m, 2H), 3.56 (d, 2H, J=5 Hz), 3.88-4.23 (m, 1H), 4.60 (bs, 2H), IR ($Cm^{-1}$): (neat) 3350, 2925, 1670, 1620, 1418, 1095, 1040

EXAMPLE 4

Synthesis of S-3,4-dihydroxy butyric acid

After dissolving 12.36 g of NaCN and 17.17 g of NaOH in 200 ml of water, 50 ml of an aqueous solution of 22.2 g of R-3-chloro-1,2-propanediol was slowly dropped while stirring for 15 hours at 80° C. After reaction, while cooling the reaction solution to 0° C., 6N HCl was added to adjust the pH to 2.5, and the volatile matter was distilled away, and $C_2H_5OH$ was added, and the precipitating solid matter was filtered. By distilling away $C_2H_5OH$ from the filtrate, a residue was obtained, and it was refined by silica gel column chromatography (hexane:acetone=1:1), and finally 15.8 g of S-3,4-dihydroxy butyric acid was obtained.

$[\alpha]_D^{20} = -27.9$ (C=0.96, $CH_3OH$)

$^1$HNMR ($CDCl_3$, $CD_3OD$): δ2.47-2.63 (m, 2H), 3.6 (d, 2H, J=5 Hz), 3.97-4.3 (m, 1H), 4.77-5.32 (m, 3H) IR ($Cm^{-1}$): (neat) 3300, 2900, 1710, 1390, 1180, 1030

REFERENCE EXAMPLE 1

Synthesis of S-3,4-dihydroxy butyric acid amide 3 g of S-3,4-dihydroxy butyronitrile was dissolved in 30 ml of 1N NaOH, and the solution was stirred for 5 hours at 40° C., and was then cooled to 0° C. while neutralizing with 2N HCl. After distilling away the volatile matter, $C_2H_5OH$ was added, and the precipitating solid matter was filtered away, and the oily matter obtained by distilling away $C_2H_5OH$ from the filtrate was refined by silica gel column chromatography (acetone), and finally 3.01 g of S-3,4-dihydroxy butyric acid amide was obtained.

REFERENCE EXAMPLE 2

Synthesis of S-3,4-dihydroxy butyric acid

Dissolving 3 g of S-3,4-dihydroxy butyronitrile in 30 ml of 2N NaOH, the solution was stirred for 6 hours at 80° C., and it was then cooled to 0° C. while adjusting the pH to 2.5 by adding 2N HCl, and by the same process as in EXAMPLE 4 thereafter, 2.92 g of S-3,4-dihydroxy butyric acid was obtained.

REFERENCE EXAMPLE 3

Synthesis of S-3,4-dihydroxy butyric acid

Dissolving 3.57 g of S-3,4-dihydroxy butyric acid amide in 40 ml of 1N NaOH, the solution was stirred for 5 hours at 80° C., and the solution was cooled to 0° C. while adjusting the pH to 2.5 by adding 2N HCl, and by the same process as in EXAMPLE 3 thereafter, 3.28 g of S-3,4-dihydroxy butyric acid was obtained.

What is claimed is:

1. A method for the preparation of S-3,4-dihydroxybutyric acid amide of structural formula (III):

$$HOCH_2 - \overset{\overset{\displaystyle OH}{|}}{\underset{\overset{\displaystyle |}{H}}{C}} - CH_2CONH_2 \qquad (III)$$

which consists essentially of reacting R-3-chloro-1,2-propanediol of structural formula (I):

$$HOCH_2 - \overset{\overset{\displaystyle OH}{|}}{\underset{\overset{\displaystyle |}{H}}{C}} - CH_2Cl \qquad (I)$$

with a metal cyanide in a solvent containing water and hydrating S-3,4-dihydroxy butyronitrile which is produced as an intermediate of the structural formula (II):

$$HOCH_2 - \overset{\overset{\displaystyle OH}{|}}{\underset{\overset{\displaystyle |}{H}}{C}} - CH_2CN \qquad (II)$$

directly with water in the solvent.

2. The method of claim 1, wherein the metal cyanide is selected from the group consisting of NaCN, KCN, $MgCN_2$, AgCN and CuCN.

3. The method of claim 1, wherein the reaction is conducted in water.

4. A method for the preparation of S-3,4-dihydroxybutyric acid of structural formula (IV):

$$HOCH_2 - \overset{\overset{\displaystyle OH}{|}}{\underset{\overset{\displaystyle |}{H}}{C}} - CH_2COOH \qquad (IV)$$

which consists essentially of reacting R-3-chloro-1,2-propanediol of structural formula (I);

$$HOCH_2 - \overset{\overset{\displaystyle OH}{|}}{\underset{\overset{\displaystyle |}{H}}{C}} - CH_2Cl \qquad (I)$$

with a metal cyanide in a solvent containing water and in the presence of a base, and directly hydrolysing the product thereof.

5. The method of claim 4, wherein the metal cyanide is selected from the group consisting of NaCN, KCN, $MgCN_2$, AgCN and CuCN.

6. The method of claim 4, wherein the reaction is conducted in the presence of NaOH, KOH or a mixture thereof in an amount equivalent to 1 or more while heating at a temperature of from 60° to 100° C.

* * * * *